(12) United States Patent
Rezvani et al.

(10) Patent No.: US 6,378,530 B1
(45) Date of Patent: Apr. 30, 2002

(54) SELF-NEUTRALIZING PERMANENT WAVE COMPOSITION AND METHOD THEREFOR

(75) Inventors: Ahmad Rezvani, Fairfield; Andrew Savaides, Norwalk; Rushi Tasker, Trumbull; Tetsuya Kambe, Darien, all of CT (US)

(73) Assignee: Shiseido Co., Ltd., Toyko (JP)

( * ) Notice: Subject to any disclaimer, the term of this patent is extended or adjusted under 35 U.S.C. 154(b) by 0 days.

(21) Appl. No.: 09/567,285

(22) Filed: May 8, 2000

(51) Int. Cl.[7] .............................. A45D 7/04; A45D 7/00; A61K 7/06; A61K 7/11
(52) U.S. Cl. ........................ 132/205; 132/202; 132/210; 424/70; 424/70.51
(58) Field of Search ................................. 132/205, 204, 132/203, 202, 210; 424/70, 70.51, 70.5, 70.2

(56) References Cited

U.S. PATENT DOCUMENTS

| | | | | |
|---|---|---|---|---|
| 5,165,427 A | * | 11/1992 | Borish | 132/204 |
| 5,208,014 A | * | 5/1993 | Dubief et al. | 424/71 |
| 5,223,252 A | * | 6/1993 | Kolc et al. | 424/72 |
| 5,260,054 A | * | 11/1993 | Nandagiri et al. | 424/71 |
| 5,332,570 A | * | 7/1994 | Bergstrom et al. | 424/72 |
| 5,639,451 A | * | 6/1997 | Evans et al. | 424/70.51 |

* cited by examiner

*Primary Examiner*—Gene Mancene
*Assistant Examiner*—Robyn Kieu Doan
(74) *Attorney, Agent, or Firm*—Melvin I. Stoltz

(57) ABSTRACT

By operationally mounting a plurality of wafers or plates forming tumblers in an independent, separate, substantially closed container, and cooperatively mounting the plate tumbler container with a cylinder forming member, a unique cylinder lock system is attained which is easily and inexpensively manufactured, as well as quickly and easily re-keyed whenever desired. In the preferred embodiment, all of the plate tumblers which are desired for the particular lock construction are mounted in the substantially closed container, with each plate tumbler having the requisite spring means associated therewith. In addition, the plate tumbler holding container incorporates one aperture for each plate tumbler which allows the slot engaging fin of each tumbler to extend outwardly from the container for locking and unlocking association with the housing.

25 Claims, No Drawings

SELF-NEUTRALIZING PERMANENT WAVE COMPOSITION AND METHOD THEREFOR

TECHNICAL FIELD

This invention relates to the art of permanently waving hair, and more particularly, to new formulations for permanent waving lotions which provide long-lasting, durable permanently waved hair while also eliminating the need for a separate oxidation or neutralization step.

BACKGROUND ART

The permanent waving of hair is a well established and well developed art in which substantial attention has been directed to improve the present level of technology. Although substantial changes have occurred throughout the last decades, various problems continue to plague the industry in spite of numerous attempts to reduce or eliminate these problems.

In order to best understand the present state of the art and the problems existing therein, it is important to reiterate that hair fibers are composed of a unique protein called "keratin" which is distinguished by the fact that it contains a very significant amount of an amino acid (cystine) which contains the element sulfur in addition to the elements nitrogen, oxygen, carbon and hydrogen. In the natural biosynthesis of hair, the element sulfur covalently links intra or inter polypeptide chains (K) through two sulfur atoms (S—S) to give keratin protein (K-S-S-K). Only by chemical action can this covalent linkage be broken.

Since these disulfide bonds are relatively strong bonds and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to reagents containing a free—SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations (i), (ii) and (iii):

  (i)

  (ii)

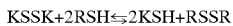  (iii)

When a sufficient number of hair disulfide bonds have been broken, the hair is realigned to pair previously unpaired hair protein thiol groups opposite opposite each other. At this point, the hair is rinsed, removing the unreacted thiol waving agent and any water soluble disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide, and can be illustrated by the following chemical reaction:

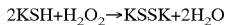

The most commonly used reducing agents employed in the permanent deformation of hair keratin are salts and esters of thioglycolic acid. Other less commonly used reducing agents include cysteine, cysteamine, thiolactic acid, their derivatives and mixtures thereof. These reducing agents are very effective in the reduction of disulfide bonds and under certain conditions can reduce more than 50% of the keratin cystine bonds.

Although effective in providing excellent reducing capabilities, the above mercaptans and their corresponding derivatives possess problems that are difficult to control. Typical disadvantages include the irreversible fiber alteration as made evident by increased fiber porosity and decreased tensile properties as well as the emission of malodor.

Much efforts have been expended in attempts to minimize these undesirable attributes. These include pretreatments, barriers which decrease the rate of diffusion, reduction of the mercaptan concentration and/or the pH of the reducing agents, and duration of reduction time. Many of these pretreatments yield other undesirable characteristics such as oily, greasy, and dirty feeling of the hair fiber.

Furthermore, in seeking to attain an improved permanent waving lotion, numerous agents have been employed in combination with the thiol compound to provide improved results. In this regard, much effort has been expended in employing numerous compounds as the alkalizing agent used in combination with the thiol compound to control the pH level as well as to reduce the malodor associated with permanent waving. As is evident from prior art disclosures, such as found in *Handbook of Cosmetic Science*, H. W. Hibbot, Ed, The MacMillan Company, New York, N.Y. 1963, Page 393–394 and *J. Soc. Cosmet. Chem.*, Garcia et al, Volume 41, Page 149 (1990), the use of alkali metal salts has been attempted and has been found to be ineffective. As disclosed in these prior art discussions, alkali metal salts, in general, and sodium hydroxide in particular, has been found to be incapable of providing a satisfactory permanently waved head of hair when combined with a thiol compound.

As a result, the cosmetic industry has sought alternate directions for creating reducing agents which principally have focused on the use of ammonia or ammonium based compounds employed in combination with the thiol compound to produce an effective permanent wave reducing agent. However, in spite of substantial effort to attain a reducing agent which can be employed with substantially less malodor being produced, these attempts have failed to provide a composition which is capable of producing a permanently waved head of hair at least equivalent to conventional reducing lotions having these inherent deficiencies.

Another major drawback that has consistently plagued prior art permanent waving systems is the requirement that a separate oxidizing or neutralizing agent must be employed after the application of the reducing lotion. The application of a separate oxidizing agent requires an additional step, as well as exposing both the beautician and the customer to further chemical exposure.

As a result, additional time is required and further chemical interaction of the hair fibers must be experienced. Although attempts have been made to eliminate the neutralization steps, these attempts have not been successful.

Furthermore, in the art of permanent waving, there is much trial and error, with the hair being over-processed, in some instances. The characteristics of over-processing are raspy feel to the hair or a loss of the natural underlying color. Structural evaluation of the hair fiber by instrumentation usually reveals that the structural integrity of the hair is lessened, which is evidenced by either an increase in the amount of cysteine and cysteic acid or a lessening of the cystine content relative to the hair not so processed. The increase in cysteic acid amount is about 15% to 25% contributed by the neutralization step.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength. Typically, in order to reshape hair fibers into a lasting configuration, 20% to 50% of available disulfide bonds must be cleaved and reformed into the new configuration. If insufficient disulfide bonds are broken, the hair fiber will rapidly regain natural configuration.

In spite of the substantial effort that has occurred in the development of various permanent waving composition of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care. In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Furthermore, permanent change in hair keratin coupled with operator error, provides inevitable damage to the hair fibers. This damage is measured by evaluating the tensile strength of hair keratin fibers caused by these chemical treatments. Therefore, it would be advantageous to provide treatments that would produce results of a permanent nature and minimum damage to hair keratin.

Since physical and chemical changes in the keratin structure of hair fibers are observed during the deformation and relaxation of hair, researchers have tried to minimize the rate of hair relaxation caused by natural forces and water, utilizing treatments of naturally occurring or synthetic polymers. Some surface polymer treatments have had temporary effect on promoting cohesion and decreasing or retarding the rate of water uptake by the hair fiber, while other treatments have attained temporary improvement of such physical characteristics as sheen, manageability and strength. However, these prior art conditioning agents merely provide a temporary benefit and are incapable of satisfying the long-felt need for substantially permanent hair condition improvement.

Therefore, it is a principal object of the present invention to provide a composition for permanently waving hair fibers which is capable of imparting to the hair a durable, long-lasting permanent hair set, while completely eliminating the need for applying an oxidizing or neutralizing agent.

Another object of the present invention is to provide a permanent wave composition having the characteristic features described above which is capable of conditioning the hair fibers and improving physical properties of the treated hair such as shine, luster, softness, manageability, hair body, and thickness.

Another object of the present invention is to provide a permanent wave composition having the characteristic features described above which is capable of imparting a long-lasting permanent wave or setting property to the hair, while substantially reducing hair damage caused by the oxidation process.

A further object of the present invention is to provide a permanent wave composition having the characteristic features described above which is capable of improving the elastic and tensile properties of the hair fibers.

Other and more specific objects will in part be obvious and will in part appear hereinafter.

DETAILED DESCRIPTION

By employing the present invention, the prior art difficulties, drawbacks, and limitations have been overcome and a long lasting, permanently waved hair is attained. Using the permanent waving composition of the present invention, the desired permanent waving of hair is achieved in a single step, with the need for the separate application of an oxidizing or neutralizing agent being completely eliminated.

In accordance with the present invention, this highly desirable, single-step permanent waving lotion is attained by combining specially paired thiols and disulfides in the single composition. As detailed below, these ingredients can be provided in the formulation as sold or, if desired, can be formed in situ, by combining two complementary agents together at the time of use.

By employing the single-step permanent waving lotion of the present invention, excellent permanent waving results are consistently attained with self-neutralization or combined reduction and oxidation. In this way, substantial benefits are realized for both the beautician and the customer, including a substantial reduction in overall processing or application time, as well as a reduction in the exposure to the chemical formulations required for the oxidation step.

In accordance with the present invention, the permanent waving lotion composition must comprise a symmetrical or unsymmetrical disulfide in combination with a thiol having an amine group. The amine group comprises one selected from the group consisting of primary amines, secondary amines, and tertiary amines. Furthermore, the thiol comprises one selected from the group consisting of cysteamine, cysteine, analogs of cysteine, cysteine methyl ester, cysteine ethyl ester and cysteine propylester. Preferably, the disulfide comprises one selected from the group consisting of cystamine and corresponding cystamine-based disulfides.

In order to best understand the unique aspects of the present invention, the preferred alternate formulations that may be employed for the thiol and the disulfide ingredients in the permanent waving lotion of this invention are detailed below as follows:

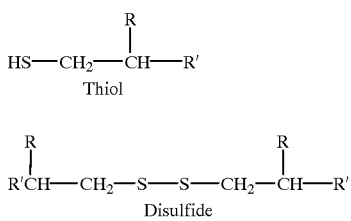

Thiol (Formula I)

Disulfide (Formula II)

where
R=H & R'=NH$_2$, or
R=H & R'=NH(CH$_3$), or
R=H & R'=N(CH$_3$)$_2$, or
R=H & R'=N(CH$_3$)$_3$+, or
R=H & R'=NH(CH$_2$CH$_3$), or
R=H & R'=N(CH$_2$CH$_3$)$_2$, or
R=H & R'=N(CH$_2$CH$_3$)$_3$+, or
R=H & R'=NH(COCH$_3$), or
R=H & R'=NH(COCH$_2$CH$_3$), or
R=NH$_2$ & R'=COOCH$_3$, or
R=NH$_2$ & R'=COOCH$_2$CH$_3$, or
R=NH$_2$ & R'=COOCH$_2$CH$_2$CH$_3$, or
R=NH$_2$ & R'=COOCH(CH$_3$)$_2$ As is evident from the foregoing, the present invention requires the combination of a thiol which is a formative of cysteamine, as defined by Formula I, while the disulfide is a formative of cystamine as defined by Formula II.

In carrying out the teaching of the present invention, the desired thiol and disulfide may be combined in a single formulation, ready for use whenever desired. Alternatively, a two-component system can be employed which are intermixed prior to use to form the desired thiol and disulfide ratio in situ.

Regardless of which system is employed, the basic permanent wave lotion of the present invention which is applied to the head of hair comprises the ingredients detailed in Table I. By employing formulations of this construction, the desired one-step, self-neutralizing permanent waving of hair is attained.

TABLE I

Permanent Wave Lotion

| Ingredient | Overall Range, % by Weight/Total Weight | Preferred Range, % by Weigh/Total Weight |
|---|---|---|
| Cysteamine-based compound as defined by Formula I | 5–25 | 6–18.75 |
| Cystamine based compound as defined by Formula II | 0.50–20 | 0.5–6.0 |
| Non-Ionic Surfactant | 1.0–5.0 | 1.0–5.0 |
| Perfume | 0.5–1.5 | 0.5–1.50 |
| Sequestering Agent | 0.10–0.50 | 0.1–0.50 |
| Ammonia 28% | q.s. for pH | q.s. for pH |
| Deionized Water | q.s. to 100% | q.s to 100% |
| pH | 7.30–8.80 | 8.0–8.6 |

As is evident from a review of Table I, the principal ingredients required for producing an effective, one-step, self-neutralizing permanent wave lotion in accordance with the present invention are fully detailed. In addition, Table I provides the overall, effective range of each ingredient, along with the preferred range for each ingredient.

In addition to employing the basic ingredients defined above in Table I, the permanent wave lotion of the present invention preferably incorporates additional additives in order to further enhance the resulting permanently waved hair as well as the comfort of the beautician and customer. In this regard, by referring to Table II, expanded, overall formulations of the permanent wave lotion of the present invention are provided, with both the overall ranges and preferred ranges for each ingredient being detailed therein.

Throughout the disclosure, chemical compounds are referred to using their generic names or using the designations adopted by the Cosmetic Toiletry and Fragrance Association (CTFA). In addition, in certain circumstances, trade names are used parenthetically.

TABLE II

Preferred Formulation for Permanent Wave Lotion

| Ingredient | Overall Range, % by Weight/Total Weight | Preferred Range, % by Weight/Total Weight |
|---|---|---|
| Cysteamine based compound as defined by Formula I | 5.00–25 | 6.00–18.75 |
| Cystamine based compound as defined by Formula II | 0.50–20 | 0.50–6.0 |
| Nonionic Surfactant | 1.0–5.0 | 1.0–5.0 |
| Perfume | 0.5–1.50 | 0.5–1.50 |
| Sequestering Agent | 0.10–0.50 | 0.10–0.50 |
| Quaternium 75 | 0.10–3.0 | 0.50–2.50 |
| Amodimethicone | 0.10–5.0 | 0.40–4.0 |
| Urea | 0.50–5.0 | 0.50–5.0 |
| Cystine Polysiloxane | 0.10–4.0 | 0.20–3.0 |
| Bisulfite | 0.01–4.0 | 0.35–2.1 |
| Ammonium Carbonate | 0.10–3.0 | 0.5–2.50 |
| Ammonium Bicarbonate | 0.10–2.5 | 0.10–2.5 |
| Deionized Water | q.s. to 100% | q.s. to 100% |
| Alkali | q.s to pH | q.s. to pH |
| pH | 7.30–8.80 | 8.0–8.6 |

As is evident from the foregoing detailed disclosure, a plurality of alternate formulations are capable of being created for the single component, one step, self-neutralizing, permanent waving lotion of the present invention. In order to provide a full disclosure of various, alternate, substantially equivalent formulations that have been attained using the teaching of the present invention, Tables III, IV, and V are provided.

In these Tables, alternate, fully formulated, permanent waving compositions are detailed, each of which has been found to provide highly desirable, effective permanent waving results. In each of the Tables provided below, as well as in all references throughout this application, the cysteamine employed is formulated as cysteamine•HCl, while the cystamine employed is formulated as cystamine•2HCl.

TABLE III

Permanent Waving Lotion

| Ingredient | % by Weight/Total Weight |
|---|---|
| Cysteamine | 11.34 |
| Cystamine | 6.75 |
| Non-Ionic Surfactant | 1.50 |
| Perfume | 0.50 |
| Sequestering agent | 0.20 |
| Ammonia 28% | q.s. to pH |

TABLE III-continued

Permanent Waving Lotion

| Ingredient | % by Weight/Total Weight |
|---|---|
| Deionized Water | q.s. to 100% |
| pH | 8.60 |

TABLE IV

Permanent Waving Lotion

| Ingredient | % by Weight/Total Weight |
|---|---|
| Cysteamine | 11.35 |
| Cystamine | 6.75 |
| Non-Ionic Surfactant | 1.50 |
| Perfume | 0.50 |
| Sequestering agent | 0.20 |
| Ethoxydiglycol | 1.00 |
| Quaternium 75 | 1.50 |
| Amodimethicone | 2.00 |
| Urea | 2.00 |
| Ammonium Bicarbonate | 1.50 |
| Ammonia 28% to | q.s. to pH |
| Deionized Water | q.s. to 100% |
| pH | 8.60 |

TABLE V

Permanent Waving Lotion

| Ingredient | % by Weight/Total Weight |
|---|---|
| Cysteamine | 15.00 |
| Cystamine | 3.00 |
| Non-Ionic Surfactant | 4.50 |
| Perfume | 1.00 |
| Sequestering agent | 0.13 |
| Glycerine | 1.5 |
| Quaternium 75 | 0.75 |
| Amodimethicone | 0.40 |
| Cystine Polysiloxane | 0.40 |
| Sodium Ascorbyl Phosphate | 0.25 |
| Bisulfite | 1.00 |
| Ammonium Carbonate | 2.00 |
| Ammonia 28% | q.s. to pH |
| Deionized Water | q.s. to 100% |
| pH | 8.10 |

By employing any of the specific formulations in Tables III, IV, or V, or by employing formulations as defined in Tables I and II, a permanent waving lotion is attained which is capable of providing permanently waved hair in a single step, without requiring the application of an oxidizing or neutralizing agent. In order to employ the teaching of the present invention and obtain the desired permanently waved head of hair, in a simple, easily achieved, one-step process, the following application method is preferably employed. Although this application method is described along with the use of permanent wave formulations of the present invention wherein all ingredients are contained into a single formulation, the same method is also employed when using the two-component wave lotion.

Prior to applying the permanent wave lotion, the head of hair is shampooed, towel dried, and wound on rollers as desired for achieving the particular curl configuration. The hair fibers are then thoroughly wetted by the permanent waving lotion of the present invention. Once all of the rolled hair fibers have been thoroughly wetted, the lotion is allowed to remain on the hair fibers for about 15 to 30 minutes, depending on the hair type, at room temperature. During this time period, no external heat is applied to the head of hair.

When the desired processing time has been completed, the hair tresses are rinsed with water for five to ten minutes, excess water is blotted, and the hair tresses are unwound from the curlers to reach the desired permanently waved style.

By employing this process using the permanent wave lotions detailed above, a permanently waved head is achieved without requiring a neutralization or oxidation step. Instead, a completely permanently waved head of hair is realized in a single step application, which achieves reduction and self-neutralization of the hair fibers in a single application. In this way, the substantial advantages detailed above are realized and the difficulties and drawbacks found in prior art systems are completely overcome.

As stated above, the one-step, self-neutralizing permanent waving lotion of the present invention can be achieved using two separate components which are intermixed to form the desired formulation. In this formulation, the thiol is contained in one of the components, while the disulfide is formed in situ as "endogenous" during the chemical reaction caused by the two components being intermixed.

In addition to forming the disulfide, the chemical reaction also causes heat to be produced. In this embodiment of the present invention, the disulfide is formed by mixing oxidants, such as hydrogen peroxide, bromates, perborates, chlorates, and persulfates with the thiol prior to application of the lotion to the hair. The following represents the reaction which forms the cystamine:

$HSCH_2CH_2NH_2$ + Oxidant ⟶
(Cysteamine)

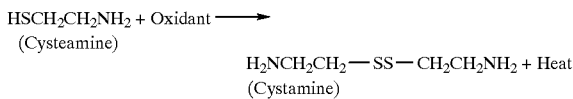
$H_2NCH_2CH_2-SS-CH_2CH_2NH_2$ + Heat
(Cystamine)

When the two-components of the present invention are intermixed, the resulting reaction produces an internal heat rise in the waving lotion which depends upon the relative amounts of the ingredients being intermixed. This heat rise typically ranges between about 20° C. and 40° C.

It has been found that improved wave performance and auto neutralization effects are best realized when the final molar ratio of cystamine to cysteamine is (0.10–1.50): 1 at a pH of between about 7.3 and 8.90. Preferably, the molar ratio is 0.50:1 and the pH ranges between 8.0 and 8.8.

By referring to Table VI, the preferred formulation for the oxidants bearing portion (portion A) of the two-component system is detailed. Although variations may be made in this formulation, the preferred composition is detailed therein.

TABLE VI

Portion A
(Oxidant Bearing Portion)

| Ingredients | % by Weight/Total Weight |
|---|---|
| Preservative | 0.05 |
| Hydrogen Peroxide | 4.33 |
| Dibasic Sodium Phosphate | 0.022 |
| Phosphoric Acid | 0.028 |
| Deionized Water | q.s. to 100% |
| pH | 3.9 |

In order to attain the desired permanent waving lotion, the second, thiol bearing portion must be intermixed with the oxidant, Portion A. In this regard, two alternate preferred compositions have been developed. These two alternate compositions are detailed below in Tables VII and VIII, with one composition being designated as Portion B and the second composition being designated as Portion C.

Although Portions B and C represent the preferred formulations for the thiol bearing portion of the two component system of the present invention, alternate compositions may be employed using the teaching of this invention. Consequently, it is intended that these formulations be considered as examples of the present invention and not as limitations thereto, with all equivalents being encompassed in the scope of this invention.

TABLE VII

Portion B
(Thiol Bearing Portion)

| Ingredients | % by Weight/Total Weight |
| --- | --- |
| Cysteamine | 19.4 |
| Non-Ionic Surfactant | 3.75 |
| Perfume | 1.25 |
| Sequestering agent | 0.13 |
| Ammonia 28% | 5.92 |
| Deionized Water | q.s. to 100% |
| pH | 8.6 |

TABLE VIII

Portion C
(Thiol Bearing Portion)

| Ingredients | % by Weight/Total Weight |
| --- | --- |
| Cysteamine | 19.4 |
| Non-Ionic Surfactant | 3.75 |
| Perfume | 1.25 |
| Sequestering agent | 0.13 |
| Ammonia 28% | 5.92 |
| Ethoxydiglycol | 1.25 |
| Quaternium 75 | 1.88 |
| Amodimethicone | 2.50 |
| Urea | 2.5 |
| Deionized Water | q.s. to 100 |
| pH | 8.6 |

In order to attain the permanent waving lotion of the present invention with the production of internal heat, Portion A is intermixed with either Portion B or Portion C. Although various mixing ratios can be employed to attain the desired permanent waving lotion, it has been found that between about 15% and 25% of the resulting mixed composition should comprise Portion A, while between about 75% and 85% of the final composition should comprise either Portion B or Portion C. In the preferred formulation, it has been found that the mixing ratio of Portion A:Portion B or Portion A:Portion C should be 20:80.

Once Portion A is intermixed with Portion B or Portion C, the chemical reaction detailed above is immediately initiated, producing the desired disulfide, along with the production of heat. The resulting composition represents this embodiment of the permanent waving lotion of the present invention. In order to assure a full and complete disclosure, Tables IX and X have been provided, wherein the resulting composition of the permanent waving lotion for each mixture is fully detailed.

TABLE IX

Permanent Waving Lotion
Portion A plus Portion B

A:B = 20:80

| Ingredients | % by Weight/Total Weight |
| --- | --- |
| Cysteamine | 11.5 |
| Cystamine | 5.5 |
| Non-Ionic Surfactant | 3.0 |
| Perfume | 1.0 |
| Sequestering agent | 0.10 |
| Ammonia 28% | 4.73 |
| Preservative | 0.04 |
| Dibasic Sodium Phos. | 0.018 |
| Phosphoric acid | 0.022 |
| Deionized water | q.s. to100 |
| pH | 8.58 |

TABLE X

Permanent Waving Lotion
(Portion A plus Portion C)

A:C = 20:80

| Ingredients | % by Weight/Total Weight |
| --- | --- |
| Cysteamine | 11.5 |
| Cystamine | 5.5 |
| Non-Ionic Surfactant | 3.0 |
| Perfume | 1.0 |
| Sequestering Agent | 0.10 |
| Ammonia 28% | 4.73 |
| Preservative | 0.04 |
| Ethoxydiglycol | 1 |
| Quaternium 75 | 1.5 |
| Amodimethicone | 2.00 |
| Urea | 2.00 |
| Dibasic Sodium Phos. | 0.018 |
| Phosphoric acid | 0.022 |
| Deionized water | q.s. to 100 |
| pH | 8.58 |

In providing the permanent waving lotion of the present invention, which is self-neutralizing and establishes a simple, easily employed formula for permanently waving hair rolled onto curlers, the waving lotion is typically formulated as a clear to opaque liquid having a viscosity similar to water. Although this formulation is preferred for application of the permanent waving lotion to hair fibers rolled on curlers, alternate formulations may be created using the teaching of the present invention for use in alternate applications. In this regard, the permanent waving lotion of the present invention may be formulated as a gel or a cream for use in permanently waving hair without curlers or for straightening hair fibers.

By referring to Table XI, an overall formulation for a rodless waving gel which is capable of permanently waving hair fibers is provided, with the range for each ingredient being detailed therein. In addition, Table XII is provided, wherein one preferred formulation for a rodless waving gel, made in accordance with the present invention, is fully detailed.

TABLE XI

Rodless Waving Gel

| Ingredient | Range % by Weight/Total Weight |
| --- | --- |
| Amodimethicone | 0.1–3.0 |
| Quaternium 75 | 0.5–2.5 |
| PVP/Dimethylamino Ethyl Methacrylate | 0.3–5.0 |

TABLE XI-continued

Rodless Waving Gel

| Ingredient | Range % by Weight/Total Weight |
|---|---|
| Copolymer (DMEAM) | |
| Cysteamine | 6.0–18.8 |
| Ammonium Carbonate | 0.5–2.5 |
| Cystamine | 0.5–5.9 |
| Bisulfite | 0.4–2.10 |
| Cystine Polysiloxane | 0.2–3.0 |
| Ammonium Hydroxide, 28% | 2.0–6.0 |
| Hydroxyethyl Cellulose | 0.5–3.5 |

TABLE XII

Rodless Waving Gel

| Ingredient | % by Wgt/Total Wgt |
|---|---|
| Carbomer | 0.50 |
| Sequestering Agent | 0.10 |
| Quaternium 75 | 0.75 |
| Glycerin | 1.50 |
| Polysorbate 20 | 0.50 |
| Amodimethicone | 0.10 |
| Cetyl Triethylmonium Dimethicone (Cetylsil) | 0.75 |
| Cysteamine | 9.00 |
| Ammonium Carbonate | 2.00 |
| Cystamine | 2.9 |
| Bisulfite | 0.70 |
| PVP/Dimethylamino Ethylmethacrylate Copolymer (PVP/DMEAM) | 0.60 |
| Cystine Polysiloxane | 0.40 |
| Hydroxyethyl Cellulose | 1.50 |
| Sodium Ascorbyl Phosphate | 0.25 |
| Non-ionic Surfactant | 1.50 |
| Perfume | 1.00 |
| Ammonia 28% | 5.00 |
| Water | q.s. to 100% |

As is evident from these tables, the rodless waving gel of the present invention incorporates both the thiol and disulfide ingredients detailed above along with the other compounds required to provide the desired enhancements and viscosity. By employing the rodless waving gel of the present invention, hair fibers can be permanently set into any desired curl or shape by merely wrapping the hair fibers, i.e., around the fingers of the beautician and applying the waving gel accordingly or applying the waving gel to the hair, shaping the hair into the desired configuration. In this way, any desired style or hair configurations are capable of being attained quickly and easily, with the resulting hair style being achieved in a manner substantially equivalent to a permanent wave.

Typically, once the waving gel has been applied to the hair and the hair has been set in the desired curl configurations, the gel is allowed to remain on the hair fibers for about 20 to 30 minutes, depending on the hair type, before thoroughly rinsing the gel from the hair fibers. Once fully rinsed, final styling and combing is employed to complete the entire process.

As is evident from the foregoing, by employing this embodiment of the present invention, a wide variety of textured hair styles can be achieved in a quick, simple, and easily applied manner. In addition, these textured hair styles are attained without requiring the hair fibers to be placed on rollers or treated with oxidizing or neutralizing agents, thereby providing expanded styling freedom and creativity without unnecessary chemical exposure.

In further expanding on the styling freedom and creativity of beauticians, the present invention has also been formulated as a relaxer for enabling hair fibers to be straightened. In addition to providing the thiol and the disulfide components detailed above, the hair relaxer of the present invention is formulated as a thick cream, for ease of application and use. As with the rodless gel formulation detailed above, the hair relaxer formulation of the present invention also provides results which are equally permanent in nature.

By referring to Table XIII, an overall formulation for the principal ingredients required to achieve a hair relaxer in accordance with the present invention is provided, with the preferred range of each ingredient being detailed therein. In addition, in Table XIV, one preferred formulation for the hair relaxer of the present invention is provided, with the preferred quantities for each ingredient listed therein.

TABLE XIII

Hair Relaxer

| Ingredient | Range % by Weight/Total Weight |
|---|---|
| Amodimethicone | 0.1–3.0 |
| Quaternium 75 | 0.5–2.5 |
| Cysteamine | 6.0–18.8 |
| Ammonium Carbonate | 0.5–2.5 |
| Cystamine | 0.5–5.9 |
| Bisulfite | 0.4–2.10 |
| Cystine Polysiloxane | 0.2–3.0 |
| Ammonium Hydroxide, 28% | 2.0–6.0 |

TABLE XIV

Hair Relaxer

| Ingredient | % by Wgt/Total Wgt |
|---|---|
| Carbomer | 0.50 |
| Sequestering Agent | 0.10 |
| Quaternium 75 | 0.75 |
| Glyceryl Stearate | 1.50 |
| Steareth 21 | 1.00 |
| Cetyl/Stearyl Alcohol | 1.50 |
| Ceteareth 20 | 1.25 |
| Amodimethicone | 0.30 |
| Cysteamine | 9.00 |
| Ammonium Carbonate | 2.00 |
| Cystamine | 2.9 |
| Bisulfite | 1.00 |
| Cystine Polysiloxane | 0.40 |
| Na Ascorbyl Phosphate | 0.25 |
| Perfume | 1.00 |
| Ammonia 28% | 5.00 |
| Water | q.s. to 100% |

In order to employ the hair relaxer of the present invention, the thick or viscous cream provided by the foregoing formulations is applied to the hair, with the hair fibers being elongated or straightened by the beauticians during the application process. Once the desired style has been attained, the hair relaxer cream is allowed to remain on the hair fibers for about 15 to 30 minutes, depending on the hair type, and then rinsed from the hair. Thereafter, the hair is combed and styled into the desired visual appearance, attaining the precisely desired hair style in a simple, easily employed, one step process, producing results which are substantially permanent.

As is evident from the foregoing detailed disclosure, the present invention achieves a wide range of varying formulations which are capable of permanently waving or styling hair fibers in a single, easily employed, one-step application process, without requiring the conventional use of an oxidation or fixation step. In this way, ease of use and reduced chemical exposure are realized, with a resulting hair fibers being permanently placed in the desired configuration.

BEST MODE FOR CARRYING OUT THE INVENTION

In order to substantiate the efficacy of combining a thiol, as defined by Formula I, with a disulfide, as defined by Formula II, in a single composition to attain the results detailed above, the following tests were conducted and examples are presented detailing the results attained. In this disclosure, the universal applicability of the present invention is fully detailed, along with the ability of the formulations of the present invention to permanently wave hair in a single, easily employed, one-step process, without requiring the separate use of oxidation or fixation agents. In addition, the following examples clearly demonstrate that the permanent waving results attained by employing the present invention are substantially equivalent to the permanent waving results attained using conventional oxidation or fixation agents.

It is to be understood, however, that the following examples are intended as a teaching of the best mode for carrying out the present invention and are not intended to limit, in any manner, the breath of this discovery. Consequently, the present invention is intended to encompass the broad range of equivalents that can be created using the overall disclosure provided herein, and no limitation on this breadth should be interpreted from the specific examples provided below.

In order to prove the efficacy of the present invention, numerous hair tresses were tested by being permanently waved using various formulations consistent with the foregoing detailed disclosure. In order to provide a standard by which the waving efficiency of the one-step permanent waving lotion of the present invention can be objectively evaluated, the "Test Tube Test Curl Method" or excess lotion method was employed.

In the Test Tube Test Curl Method (TTTC), 12 hair fibers are knotted at the root end and cut to a length of 4.5 inches from the knot. The bundle is immersed in water and then wound around a glass mandrel having a diameter of 7.0 mm. The mandrel is placed in a test tube containing 5 ml of the permanent waving lotion.

Then, the test tube is capped with Parafilm and immersed into a water bath maintained at a constant temperature, usually 37° C., for the prescribed processing time. Once completed, the permanent waving lotion is drained off, and the test tube and its contents are rinsed three times with water. Thereafter, the bundle is removed from the mandrel and both the length and diameter of the resulting curl is recorded.

An acceptable curl has a curl diameter (D) ranging between about 8.0 and 10.5 mm, and a coil length (L) ranging between about 35 and 60 mm. The "deficiency in wave tightness" or D.I.W.T. is calculated as follows:

$$DIWT = \frac{\text{diameter of hair coil (MM)} - \text{diameter mandrel (MM)}}{\text{diameter of mandrel (MM)}} \times 100$$

The D.I.T. or D.I.W.T. is a measurement of the waving efficiency of the permanent waving lotion. Excellent curls typically have a DIWT ranging between about 14 and 30.0. Curls with DIWT greater than 70 are cosmetically unacceptable.

In addition, the efficacy of the permanent waving lotion of the present invention was also evaluated using the Tress Strand Method. By employing the Tress Strand Method, the amount of curvature of the hair fiber which is attained by the permanent waving lotion is able to be determined.

In using the Tress Strand Method, several tresses of hair fibers are selected and permanently waved using the process detailed below. Prior to the application of the permanent wave lotion to the hair tresses, the length of each hair tress is measured and recorded. About 2.5 g of lightly wet, chemically untreated fibers of 8" (203.2 mm) length are rolled onto a rod of 16.70 mm diameter and then followed with perming. The hair tresses were processed for 20 minutes followed with or without 5 minutes neutralization. Then, after treatment, the length of the resulting tresses are measured, along with the number of crests. The curvature is determined from the following formula:

$$\text{Curvature} = \frac{\text{(Initial length of hair tresses)} \times \text{(number of crests)}}{\text{Length of Treated Hair Tress}}$$

An acceptable curl will have a curvature value from about 3 to 10. Curvature values of less than 3.5 are cosmetically unacceptable.

EXAMPLES

In order to demonstrate the efficacy of the present invention, numerous hair tresses were tested using the methods detailed above for conducting the Tress Strand Method and the Test Tube Test Curl Method. In each instance, numerous hair tresses were subjected to the conditions specified, and the overall average was computed and reported. By referring to Tables XV and XVI, the results obtained from these tests are fully detailed.

In these tests, the permanent wave lotion defined in Table IIII was employed as the basic lotion formulation. However, as clearly detailed in the Tables, the molar ratio of the cystamine to cysteamine was varied for comparative purposes. In addition, the weight ratio of the cystamine to the cysteamine is also provided in Tables XV and XVI. Finally, for purposes of comparison, a conventional permanent wave formulation was employed as a control and the test results for this product are also provided. Based on the data of Table XV, the optimum wave performance of cystamine:cysteamine mixtures is from (0.30–0.5):1 molar ratio. This is depicted by the tightness of the curl (DIWT) and hair damage (20% Index).

TABLE XV

Test Tube Test Curl (TTTC) Wave Performance
Evaluation of Cystamine/Cysteamine Mixtures
Using Composition of Table III

| Examples | Molar Ratio Cysta: Cysteam | % Wt/Wt Cysta: Cysteam | d(mm) | l(mm) | 20% Index | DIWT |
|---|---|---|---|---|---|---|
| 1 | 0.1:1 | 2.25:11.35 | 9.81 | 55.55 | 0.760 | 40.14 |
| 2 | 0.30:1 | 5.75:11.35 | 9.43 | 49.59 | 0.797 | 34.71 |
| 3 | 0.50:1 | 11.25:11.35 | 9.16 | 48.61 | 0.779 | 30.86 |
| 4 | 1.00:1 | 22.5:11.35 | 8.75 | 47.43 | 0.772 | 25.00 |
| 5 | 1.5:1 | 33.25:11.35 | 9.3 | 49.58 | 0.747 | 32.86 |
| 6 | control | 11.35 | 10.23 | 54.33 | 0.764 | 46.14 |

TABLE XVI

Tress Strand Method (TSM) Wave Performance
Evaluation of Cystamine/Cysteamine Mixtures
Using Composition of Table III

| Examples | Molar Ratio Cysta:Cysteam | % Wt/Wt Cysta:Cysteam | Curvature | % Water Retention |
|---|---|---|---|---|
| 1 | 0.1:1 | 2.25:11.35 | 6.15 | 20.03 |
| 2 | 0.30:1 | 6.75:11.35 | 6.50 | 18.83 |
| 3 | 0.50:1 | 11.25:11.35 | 6.58 | 15.85 |
| 4 | 1.00:1 | 22.5:11.35 | 6.58 | 19.24 |
| 5 | 1.5:1 | 33.25:11.35 | 6.18 | 14.40 |
| 6 | control | 0:11.35 | 4.81 | 27.18 |

In order to further demonstrate the ability of the permanent wave lotion of the present invention to provide highly desirable permanent waving results without the need for neutralization, numerous additional tests were conducted with varying molar ratios of cystamine to cysteamine, based upon the composition defined in Table III. In these tests, each formulation was subjected to a neutralization step, as well as being performed without neutralization. The results of this series of tests are detailed in Table XVII, along with the results of a conventional permanent waving lotion.

TABLE XVII

Tress Strand Method (TSM), Wave Performance Evaluation
of Cystamine/Cysteamine Mixtures

| Example | Molar Ratio | Disulfide | Thiol | pH | Neutralization | Index of Fixation | Curvature | 20% Index |
|---|---|---|---|---|---|---|---|---|
| 7 | 0.30:1 | Cystamine | Cysteamine | 8.50 | Yes | 0.020 | 6.11 | — |
| 8 | 0.30:1 | Cystamine | Cysteamine | 8.50 | No | 0.017 | 5.54 | — |
| 9 | 0.50:1 | Cystamine | Cysteamine | 8.50 | Yes | 0.015 | 6.48 | 0.751 |
| 10 | 0.50:1 | Cystamine | Cysteamine | 8.50 | No | 0.019 | 5.28 | 0.832 |
| 11 | 0.00:1 | Cystamine | Cysteamine | 8.50 | Yes | 0.027 | 6.54 | 0.836 |
| 12 | 0.00:1 | Cystamine | Cysteamine | 8.50 | No | 0.16 | 4.67 | |
| 13 | 0.30:1 | DTGA | TGA | 9.10 | Yes | 0.024 | 7.11 | 0.803 |
| 14 | 0.30:1 | DTGA | TGA | 9.10 | No | 0.247 | 3.21 | 0.778 |

Note: Cysteamine/Cystamine mixtures were prepared using composition of Table III In addition to providing the resulting data for the Tress Strand Method, Table XVII also provides the data obtained by determining the Index of Fixation for each formulation. The index of fixation value is one of the criteria for permanent wave performance. Acceptable perming is attained when the index of fixation value is 0.1 or less. Index of fixation values of greater than 0.1 predict unacceptable perming or insufficient reconstruction of S—S bridges in hair. In determining the Index of Fixation for each permanent wave lotion, the following formula was employed:

$$\text{Index of fixation} = \frac{F_3 - F_2}{F_1 - F_2}$$

where $F_1$ = plasticity force (force at 5% to 25% extension) before treatment
$F_2$ = plasticity force without neutralization
$F_3$ = plasticity force after neutralization In order to provide further comparative analysis, additional tests were conducted using cystamine as the disulfide in combination with numerous, different, conventional mercaptans. Each permanent waving formulation was performed with conventional neutralization, as well as with the neutralization step omitted. The resulting data obtained from this group of tests is detailed in Table XVIII.

TABLE XVIII

Tress Strand Method (TSM), Wave Performance Evaluation
of Cystamine/Mercaptan Mixtures

| Examples | Molar Ratio | Disulfide: Thiol | pH | Neutralization | Curvature |
|---|---|---|---|---|---|
| 15 | 0.30:1 | Cystamine:ATGA | 9.10 | Yes | 5.71 |
| 16 | 0.30:1 | Cystamine:ATGA | 9.10 | No | 2.13 |
| 17 | 0.30:1 | Cystamine:GMT | 7.80 | Yes | 4.73 |
| 18 | 0.30:1 | Cystamine:GMT | 7.80 | No | 2.24 |
| 19 | 0.30:1 | Cystamine:Ethyl Cysteine | 8.00 | Yes | 4.66 |
| 20 | 0.30:1 | Cystamine:Ethyl Cysteine | 8.00 | No | 4.67 |
| 21 | 0.30:1 | Cystamine:NH4 Bisulfite | 7.00 | Yes | 3.30 |
| 22 | 0.30:1 | Cystamine:NH4 Bisulfite | 7.00 | No | 1.03 |
| 23 | 0.30:1 | Cystamine:Cysteine | 9.00 | Yes | 2.99 |
| 24 | 0.30:1 | Cystamine:Cysteine | 9.00 | No | 2.10 |

TABLE XVIII-continued

Tress Strand Method (TSM), Wave Performance Evaluation
of Cystamine/Mercaptan Mixtures

| Examples | Molar Ratio | Disulfide: Thiol | pH | Neutralization | Curvature |
|---|---|---|---|---|---|
| 25 | 0.30:1 | Cystamine:Methyl Cysteine | 8.50 | Yes | 5.75 |
| 26 | 0.30:1 | Cystamine:Methyl Cysteine | 8.50 | No | 5.98 |

The final group of tests which were conducted compared the wave producing performance of the various different formulations detailed above for the permanent wave lotion of the present invention. Each of the formulations defined in Tables IIII, IV, V, IX, and X were prepared and tested using the methods detailed above for the Tress Strand Method and the Test Tube Test Curl Method. In each instance, each formulation was tested in accordance with the present invention, without neutralization, as well as with neutralization for comparative purposes. The results obtained from this series of tests are detailed in Table XIX.

TABLE XIX

Wave Performance of Composition Formulas

| Examples | 33 | 34 | 35 | 36 | 27 | 28 | 29 | 30 | 31 | 32 |
|---|---|---|---|---|---|---|---|---|---|---|
| Composition Table | IX | IX | X | X | III | III | IV | IV | V | V |
| Processing Time | 20 min | 20 min | 20 min | 20 min | 20 min | 20 min | 20 min | 20 min | 20 min | 20 min |
| Neutralization | 5 min | None | 5 min | None | 5 min | None | 5 min | None | 5 min | None |
| Tress Strand Method Curvature | 6.11 | 5.54 | 5.96 | 5.91 | 5.80 | 5.72 | 6.05 | 5.92 | 5.00 | 6.11 |
| Processing Time | 10 min | 10 min | 10 min | 10 min | 10 min | 10 min | 10 min | 10 min | 10 min | 10 min |
| Neutralization Time | 5 min | None | 5 min | None | 5 min | None | 5 min | None | 5 min | None |
| Test Tube Test Curl diameter (mm) | 9.14 | 10.40 | 9.01 | 10.33 | 9.50 | 10.58 | 9.30 | 10.6 | | |
| Length (mm) | 46.63 | 47.20 | 45.10 | 46.63 | 47.30 | 46.75 | 46.10 | 46.73 | | |
| DIW | 30.57 | 48.57 | 28.71 | 47.57 | 35.71 | 51.14 | 32.86 | 51.43 | | |
| % Curl Retention | 94.27 | 90.73 | | | | | | | | |

As detailed above, the formulation of the permanent wave lotions defined in Tables IX and X also produce heat as part of the reaction of Portion A with either Portion B or Portion C. By referring to Tables XX and XXI, the temperature rise experienced in the resulting permanent wave lotion for each of these compositions is fully detailed.

TABLE XX

Heat Rise in Combination of Compositions of Table VI with Table VII

| Time | Temperature C. |
|---|---|
| 0 after mixing | 22.5 |
| 20 sec. | 42.5 |
| 2 min. | 40.5 |
| 5 min. | 39 |
| 7 min. | 38 |
| 10 min. | 36 |
| 15 min. | 35 |
| 20 min. | 33 |
| 30 min. | 30 |

TABLE XXI

Heat Rise in Combination of Compositions of Table VI with Table VIII

| Time | Temperature C. |
|---|---|
| 0 after mixing | 22.5 |
| 20 sec. | 42.5 |
| 2 min. | 40.5 |
| 5 min. | 39 |
| 7 min. | 38 |
| 10 min. | 36 |
| 15 min. | 35 |
| 20 min. | 33 |
| 30 min. | 30 |

As is evident from the foregoing disclosure and test data, the permanent waving lotions of the present invention are capable of providing a highly desirable, permanent wave in a simple, easily employed one-step process, without requiring the use of an oxidizing or neutralizing agent. As is evident from the foregoing disclosure, the resulting permanent waved hair is equivalent to or better than the results attained using conventional formulations and processes, while eliminating extra steps and unnecessary chemical exposure.

It will thus be seen that the objects set forth above, among those made apparent from the preceding description, are efficiently attained and, since certain changes may be made in the compositions detailed herein, as well as in carrying out the above process, without departing from the scope of the invention, it is intended that all matter contained in the above description shall be interpreted as illustrative and not in a limiting sense.

It is to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients whenever the sense permits.

Having described our invention, what we claim as new and desire to secure by Letters Patent is:

1. A permanent waving composition for reducing and neutralizing hair fibers in a single application, said composition comprising a thiol which is a cysteamine or its analog as defined by Formula I and a disulfide which is a cystamine or its analog as defined by Formula II in accordance with the following:

Formula I

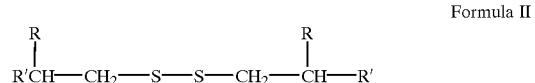

Formula II where
R=H & R'=$NH_2$, or
R=H & R'=$NH(CH_3)$, or
R=H & R'=$N(CH_3)_2$, or
R=H & R'=$N(CH_3)_3$+, or
R=H & R'=$NH(CH_2CH_3)$, or
R=H & R'=$N(CH_2CH_3)_2$, or
R=H & R'=$N(CH_2CH_3)_3$+, or
R=H & R'=N $H(COCH_3)$, or
R=H & R'=$NH(COCH_2CH_3)$, or
R=$NH_2$ & R'=$COOCH_3$, or
R=$NH_2$ & R'=$COOCH_2CH_3$, or
R=$NH_2$ & R'=$COOCH_2CH_2CH_3$, or
R=$NH_2$ & R'=$COOCH(CH_3)_2$.

2. A permanent waving composition for reducing and neutralizing hair fibers in a single step, self-neutralizing composition, said composition comprising:

A. between about 5% and 25% by weight based upon the weight of the entire composition of a cysteamine-based compound or its analog as defined by Formula I

FORMULA I

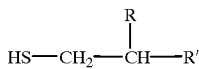

where
R=H & R'=NH$_2$, or
R=H & R'=NH(CH$_3$), or
R=H & R'=N(CH$_3$)$_2$, or
R=H & R'=N(CH$_3$)$_3$+, or
R=H & R'=NH(CH$_2$CH$_3$), or
R=H & R'=N(CH$_2$CH$_3$)$_2$, or
R=H & R'=N(CH$_2$CH$_3$)$_3$+, or
R=H & R'=NH(COCH$_3$), or
R=H & R'=NH(COCH$_2$CH$_3$), or
R=NH$_2$ & R'=COOCH$_3$, or
R=NH$_2$ & R'=COOCH$_2$CH$_3$, or
R=NH$_2$ & R'=COOCH$_2$CH$_2$CH$_3$, or
R=NH$_2$ & R'=COOCH(CH$_3$)$_2$;

B. between about 0.50% and 20% by weight based upon the weight of the entire composition of a cystamine-based compound or its analog as defined by Formula II

FORMULA II

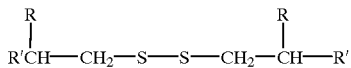

where
R=H & R'=NH$_2$, or
R=H & R'=NH(CH$_3$), or
R=H & R'=N(CH$_3$)$_2$, or
R=H & R'=N(CH$_3$)$_3$+, or
R=H & R'=NH(CH$_2$CH$_3$), or
R=H & R'=N(CH$_2$CH$_3$)$_2$, or
R=H & R'=N(CH$_2$CH$_3$)$_3$+, or
R=H & R'=NH(COCH$_3$), or
R=H & R'=NH(COCH$_2$CH$_3$), or
R=NH$_2$ & R'=COOCH$_3$, or
R=NH$_2$ & R'=COOCH$_2$CH$_3$, or
R=NH$_2$ & R'=COOCH$_2$CH$_2$CH$_3$, or
R=NH$_2$ & R'=COOCH(CH$_3$)$_2$;

C. between about 1% and 5% by weight based upon the weight of the entire composition of a non-ionic surfactant;

D. between about 0.5% and 1.5% by weight based upon the weight of the entire composition of a perfume;

E. between about 0.10% and 0.50% by weight based upon the weight of the entire composition of a sequestering agent;

F. an alkalizing agent in sufficient amount to establish the pH of the composition in a range between about 7.30 and 8.80; and G. deionized water forming the balance.

3. The permanent waving composition defined in claim 2, wherein said single-step, self-neutralizing composition comprises:

A. between about 6% and 18.75% by weight based upon the weight of the entire composition of a cysteamine-based compound as defined by Formula I;

B. between about 0.5% and 6% by weight based upon the weight of the entire composition of a cystamine-based compound as defined by Formula II;

C. between about 1% and 5% by weight based upon the weight of the entire composition of a non-ionic surfactant;

D. between about 0.5% and 1.50% by weight based upon the weight of the entire composition of a perfume;

E. between about 0.1% and 0.50% by weight based upon the weight of the entire composition of a sequestering agent;

F. an alkalizing agent in sufficient amount to establish the pH of the composition in a range between about 8.0 and 8.6; and G. deionized water forming the balance.

4. The permanent waving composition defined in claim 2, wherein said single-step, self-neutralizing composition further comprises:

H. between about 0.10% and 3.0% by weight based upon the weight of the entire composition of quarternium 75;

I. between about 0.10% and 5.0% by weight based upon the weight of the entire composition of amodimethicone;

J. between about 0.50% and 5.0% by weight based upon the weight of the entire composition of urea;

K. between about 0.10% and 4.0% by weight based upon the weight of the entire composition of cystine polysiloxane;

L. between about 0.01% and 4.0% by weight based upon the weight of the entire composition of bisulfite;

M. between about 0.10% and 3.0% by weight based upon the weight of the entire composition of ammonium carbonate; and N. between about 0.10% and 2.5% by weight based upon the weight of the entire composition of ammonium bicarbonate.

5. The permanent waving composition defined in claim 4, wherein said composition further comprises:

H. between about 0.50% and 2.50% by weight based upon the weight of the entire composition of quarternium 75;

I. between about 0.40% and 4.0% by weight based upon the weight of the entire composition of amodimethicone;

J. between about 0.50% and 5.0% by weight based upon the weight of the entire composition of urea;

K. between about 0.20% and 3.0% by weight based upon the weight of the entire composition of cystine polysiloxane;

L. between about 0.35% and 2.1% by weight based upon the weight of the entire composition of bisulfite;

M. between about 0.50% and 2.50% by weight based upon the weight of the entire composition of ammonium carbonate; and N. between about 0.10% and 2.5% by weight based upon the weight of the entire composition of ammonium bicarbonate.

6. The permanent waving composition defined in claim 1, wherein said composition is further defined as comprising:

A. about 11.34% by weight based upon the weight of the entire composition of cysteamine•HCl;
B. about 6.75% by weight based upon the weight of the entire composition of cystamine•2HCl;
C. about 1.50% by weight based upon the weight of the entire composition of non-ionic surfactant;
D. about 0.50% by weight based upon the weight of the entire composition of perfume;
E. about 0.20% by weight based upon the weight of the entire composition of sequestering agent;
F. ammonia (28%) in sufficient quantity to establish the pH of the composition at 8.60; and
G. deionized water forming the balance.

7. The permanent waving composition defined in claim 1, wherein said composition is further defined as comprising:
A. about 11.35% by weight based upon the weight of the entire composition of cysteamine•HCl;
B. about 6.75% by weight based upon the weight of the entire composition of cystaminee•2HCl;
C. about 1.50% by weight based upon the weight of the entire composition of non-ionic surfactant;
D. about 0.50% by weight based upon the weight of the entire composition of perfume;
E. about 0.20% by weight based upon the weight of the entire composition of sequestering agent;
F. about 1.00% by weight based upon the weight of the entire composition of ethoxydiglycol;
G. about 1.50% by weight based upon the weight of the entire composition of quaternium 75;
H. about 2.00% by weight based upon the weight of the entire composition of amodimethicone;
I. about 2.00% by weight based upon the weight of the entire composition of urea;
J. about 1.50% by weight based upon the weight of the entire composition of ammonium bicarbonate;
K. ammonia (28%) in sufficient quantity to establish the pH of the composition at 8.60; and
L. deionized water forming the balance.

8. The permanent waving composition defined in claim 1, wherein said composition is further defined as comprising:
A. about 15% by weight based upon the weight of the entire composition of cysteamine•HCl;
B. about 3% by weight based upon the weight of the entire composition of cystamine•2HCl;
C. about 4.50% by weight based upon the weight of the entire composition of non-ionic surfactant;
D. about 1% by weight based upon the weight of the entire composition of perfume;
E. about 0.13% by weight based upon the weight of the entire composition of sequestering agent;
F. about 1.5% by weight based upon the weight of the entire composition of glycerine;
G. about 0.75% by weight based upon the weight of the entire composition of quaternium 75;
H. about 0.40% by weight based upon the weight of the entire composition of amodimethicone;
I. about 0.40% by weight based upon the weight of the entire composition of cystine polysiloxane;
J. about 0.25% by weight based upon the weight of the entire composition of sodium ascorbyl phosphate;
K. about 1% by weight based upon the weight of the entire composition of bisulfite;
L. about 2% by weight based upon the weight of the entire composition of ammonium bicarbonate;
M. ammonia (28%) in sufficient quantity to establish the pH of the composition at 8.10; and
N. deionized water forming the balance.

9. A permanent wave composition for reducing and neutralizing hair fibers in a single application, said composition comprising a first portion and a second portion which are intermixed prior to use and produce a disulfide and heat when intermixed said first portion incorporating at least one oxidant and said second portion incorporating a thiol which is a cysteamine-based compound or its analog as defined by Formula I

FORMULA I

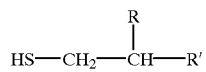

where
R=H & R'=$NH_2$, or
R=H & R'=$NH(CH_3)$, or
R=H & R'=$N(CH_3)_2$, or
R=H & R'=$N(CH_3)_3+$, or
R=H & R'=$NH(CH_2CH_3)$, or
R=H & R'=$N(CH_2CH_3)_2$, or
R=H & R'=$N(CH_2CH_3)_3+$, or
R=H & R'=$NH(COCH_3)$, or
R=H & R'=$NH(COCH_2CH_3)$, or
R=$NH_2$ & R'=$COOCH_3$, or
R=$NH_2$ & R'=$COOCH_2CH_3$, or
R=$NH_2$ & R'=$COOCH_2CH_2CH_3$, or
R=$NH_2$ & R'=$COOCH(CH_3)_2$ and the disulfide produced is a cystamine-based compound or its analog as defined by Formula II

FORMULA II

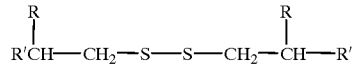

where
R=H & R'=$NH_2$, or
R=H & R'=$NH(CH_3)$, or
R=H & R'=$N(CH_3)_2$, or
R=H & R'=$N(CH_3)_3+$, or
R=H & R'=$NH(CH_2CH_3)$, or
R=H & R'=$N(CH_2CH_3)_2$, or
R=H & R'=$N(CH_2CH_3)_3+$, or
R=H & R'=$NH(COCH_3)$, or
R=H & R'=$NH(COCH_2CH_3)$, or
R=$NH_2$ & R'=$COOCH_3$, or
R=$NH_2$ & R'=$COOCH_2CH_3$, or
R=$NH_2$ & R'=$COOCH_2CH_2CH_3$, or
R=$NH_2$ & R'=$COOCH(CH_3)_2$.

10. The permanent wave composition defined in claim 9, wherein said first portion comprises:
A. about 4.33% by weight based upon the weight of the entire composition of hydrogen peroxide;
B. about 0.05% by weight based upon the weight of the entire composition of preservative;

C. about 0.022% by weight based upon the weight of the entire composition of dibasic sodium phosphate;
D. about 0.028% by weight based upon the weight of the entire composition of phosphoric acid;
E. deionized water forming the balance; and
F. a pH of about 3.9.

11. The permanent wave composition defined in claim 10, wherein said second portion comprises:
A. about 19.4% by weight based upon the weight of the entire composition of cysteamine•HCl;
B. about 3.75% by weight based upon the weight of the entire composition of non-ionic surfactant;
C. about 1.25% by weight based upon the weight of the entire composition of perfume;
D. about 0.13% by weight based upon the weight of the entire composition of sequestering agent;
E. ammonia (28%) in sufficient quantity to establish the pH of the composition at 8.6; and
F. deionized water forming the balance.

12. The permanent wave composition defined in claim 10, wherein said second portion comprises:
A. about 19.4% by weight based upon the weight of the entire composition of cysteamine•HCl;
B. about 3.75% by weight based upon the weight of the entire composition of non-ionic surfactant;
C. about 1.25% by weight based upon the weight of the entire composition of perfume;
D. about 0.13% by weight based upon the weight of the entire composition of sequestering agent;
E. ammonia (28%) in sufficient quantity to establish the pH of the composition at 8.60;
F. about 1.25% by weight based upon the weight of the entire composition of ethoxydiglycol;
G. about 1.88% by weight based upon the weight of the entire composition of quaternium 75;
H. about 2.50% by weight based upon the weight of the entire composition of amodimethicone;
I. about 2.5% by weight based upon the weight of the entire composition of urea; and
J. deionized water forming the balance.

13. The permanent wave composition defined in claim 9, wherein between about 15% and 25% by weight, based upon the weight of the intermixed composition, of the first portion is intermixed with between about 75% and 85% by weight, based upon the weight of the intermixed composition, of the second portion.

14. The permanent wave composition defined in claim 13, wherein the mixing ratio of the first portion to the second portion is further defined as comprising 20:80.

15. The permanent wave composition defined in claim 9, wherein the molar ratio of cystamine to cysteamine in the mixed composition ranges between about 0.10–1.50 to 1.0, at a pH of between about 7.3 and 8.90.

16. The permanent wave composition defined in claim 1, wherein said composition is formulated as one selected from the group consisting of a permanent wave lotion for use with curling rods, a rodiess permanent waving gel, and a rodless straightening cream.

17. The permanent wave composition defined in claim 1, wherein said composition is formulated as a gel for permanently waving hair without the use of rods and comprises:
A. between about 6% and 18.8% by weight based upon the weight of the entire composition of cysteamine•HCl;
B. between about 0.5% and 5.9% by weight based upon the weight of the entire composition of cystamine•2HCl;
C. between about 0.1% and 3% by weight based upon the weight of the entire composition of amodimethicone;
D. between about 0.5% and 2.5% by weight based upon the weight of the entire composition of quaternium 75;
E. between about 0.3% and 5% by weight based upon the weight of the entire composition of PVP/Dimethylamino ethyl methacrylate copolymer;
F. between about 0.5% and 2.5% by weight based upon the weight of the entire composition of ammonium carbonate;
G. between about 0.4% and 2.10% by weight based upon the weight of the entire composition of bisulfite;
H. between about 0.2% and 3% by weight based upon the weight of the entire composition of cystine polysiloxane;
I. between about 2% and 6% by weight based upon the weight of the entire composition of ammonium hydroxide (28%); and
J. between about 0.5% and 3.5% by weight based upon the weight of the entire composition of hydroxyethyl cellulose.

18. The permanent wave composition defined in claim 1, wherein said composition is formulated as a permanent hair straightener or relaxer and comprises:
A. between about 6% and 18.8% by weight based upon the weight of the entire composition of cysteamine•HCl;
B. between about 0.5% and 5.9% by weight based upon the weight of the entire composition of cystamine•2HCl;
C. between about 0.1% and 3% by weight based upon the weight of the entire composition of amodimethicone;
D. between about 0.5% and 2.5% by weight based upon the weight of the entire composition of quaternium 75;
E. between about 0.5% and 2.5% by weight based upon the weight of the entire composition of ammonium carbonate;
F. between about 0.4% and 2.10% by weight based upon the weight of the entire composition of bisulfite;
G. between about 0.2% and 3% by weight based upon the weight of the entire composition of cystine polysiloxane; and
H. between about 2% and 6% by weight based upon the weight of the entire composition of ammonium hydroxide (28%).

19. A method for permanently waving hair comprising the steps of:
A. shampooing the head of hair;
B. towel blotting the hair;
C. winding the hair fibers onto rollers for achieving the desired curl configuration;
D. applying the permanent wave lotion to the hair wound on the rollers, said permanent wave lotion comprising a thiol which is a cysteamine or its analog as defined by Formula I and a disulfide which is a cystamine or its analog as defined by Formula II in accordance with the following:

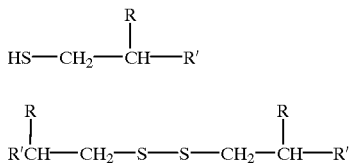

Formula I

Formula II where
R=H & R'=NH$_2$, or
R=H & R'=NH(CH$_3$), or
R=H & R'=N(CH$_3$)$_2$, or
R=H & R'=N(CH$_3$)$_3$+, or
R=H & R'=NH(CH$_2$CH$_3$), or
R=H & R'=N(CH$_2$CH$_3$)$_2$, or
R=H & R'=N(CH$_2$CH$_3$)$_3$+, or
R=H & R'=NH(COCH$_3$), or
R=H & R'=NH(COCH$_2$CH$_3$), or
R=NH$_2$ & R'=COOCH$_3$, or
R=NH$_2$ & R'=COOCH$_2$CH$_3$, or
R=NH$_2$ & R'=COOCH$_2$CH$_2$CH$_3$, or
R=NH$_2$ & R'=COOCH(CH$_3$)$_2$ E. allowing a time period ranging between about 15 minutes and 30 minutes to lapse at room temperature after the hair fibers have been thoroughly wetted by the permanent waving lotion;

F. thoroughly rinsing the hair for between about 5 and 10 minutes and then removing the rollers from the hair fiber; and G. combing the permanently waived hair in the desired style.

20. The process defined in claim 19, wherein the permanent wave lotion is prepared by mixing a first oxidant bearing portion with a second thiol bearing portion to attain the desired intermixed permanent wave lotion.

21. The process defined in claim 20, wherein the first oxidant bearing portion comprises:

A. about 4.33% by weight based upon the weight of the entire composition of hydrogen peroxide;

B. about 0.05% by weight based upon the weight of the entire composition of preservative;

C. about 0.022% by weight based upon the weight of the entire composition of dibasic sodium phosphate;

D. about 0.028% by weight based upon the weight of the entire composition of phosphoric acid;

E. deionized water forming the balance; and

F. a pH of about 3.9.

22. The process defined in claim 21, wherein said second thiol bearing portion comprises:

A. about 19.4% by weight based upon the weight of the entire composition of cysteamine•HCl;

B. about 3.75% by weight based upon the weight of the entire composition of a non-ionic surfactant;

C. about 1.25% by weight based upon the weight of the entire composition of perfume;

D. about 0.13% by weight based upon the weight of the entire composition of a sequestering agent;

E. ammonia (28%) in sufficient quantity to establish the pH of the composition at 8.6; and F. deionized water forming the balance.

23. The process defined in claim 22, wherein said second thiol bearing portion comprises:

A. about 19.4% by weight based upon the weight of the entire composition of cysteamine•HCl;

B. about 3.75% by weight based upon the weight of the entire composition of non-ionic surfactant;

C. about 1.25% by weight based upon the weight of the entire composition of perfume;

D. about 0.13% by weight based upon the weight of the entire composition of sequestering agent;

E. ammonia (28%) in sufficient quantity to establish the pH of the composition at 8.60;

F. about 1.25% by weight based upon the weight of the entire composition of ethoxydiglycol;

G. about 1.88% by weight based upon the weight of the entire composition of quaternium 75;

H. about 2.50% by weight based upon the weight of the entire composition of amodimethicone;

I. about 2.5% by weight based upon the weight of the entire composition of urea; and J. deionized water forming the balance.

24. A method for permanently waving hair without employing curlers or rollers comprising the steps of:

A. shampooing the head of hair;

B. towel blotting the head of hair;

C. applying a permanent waving gel to the hair fibers, said permanent waving gel comprising:
  a. between about 6% and 18.8% by weight based upon the weight of the entire composition of cysteamine•HCl;
  b. between about 0.5% and 5.9% by weight based upon the weight of the entire composition of cystamine•2HCl;
  c. between about 0.1% and 3% by weight based upon the weight of the entire composition of amodimethicone;
  d. between about 0.5% and 2.5% by weight based upon the weight of the entire composition of quaternium 75;
  e. between about 0.3% and 5% by weight based upon the weight of the entire composition of PVP/Dimethylamino ethyl methacrylate copolymer;
  f. between about 0.5% and 2.5% by weight based upon the weight of the entire composition of ammonium carbonate;
  g. between about 0.4% and 2.10% by weight based upon the weight of the entire composition of bisulfite;
  h. between about 0.2% and 3% by weight based upon the weight of the entire composition of cystine polysiloxane;
  i. between about 2% and 6% by weight based upon the weight of the entire composition of ammonium hydroxide (28%); and
  j. between about 0.5% and 3.5% by weight based upon the weight of the entire composition of hydroxyethyl cellulose;

D. repeatedly winding the hair fibers of the head of hair around the fingers of an individual to achieve the desired curl configuration;

E. allowing a time period ranging between about 15 minutes and 30 minutes to lapse at room temperature after the head of hair has been placed in the desired curl configuration;

F. rinsing the head of hair; and

G. combing the permanently waved hair in the desired style.

25. A method for straightening or relaxing hair comprising the steps of:
   A. shampooing the head of hair;
   B. towel blotting the head of hair;
   C. applying a hair straightening/relaxing cream to the hair fibers on which straightening is desired, said hair relaxing/hair straightening composition comprising:
      a. between about 6% and 18.8% by weight based upon the weight of the entire composition of cysteamine•HCl;
      b. between about 0.5% and 5.9% by weight based upon the weight of the entire composition of cystamine•2HCl;
      c. between about 0.1% and 3% by weight based upon the weight of the entire composition of amodimethicone;
      d. between about 0.5% and 2.5% by weight based upon the weight of the entire composition of quaternium 75;
      e. between about 0.5% and 2.5% by weight based upon the weight of the entire composition of ammonium carbonate;
      f. between about 0.4% and 2.10% by weight based upon the weight of the entire composition of bisulfite;
      g. between about 0.2% and 3% by weight based upon the weight of the entire composition of cystine polysiloxane; and
      h. between about 2% and 6% by weight based upon the weight of the entire composition of ammonium hydroxide (28%);
   D. simultaneously combing and straightening in the hair fibers to attain the desired style;
   E. allowing a time period ranging between about 15 minutes and 30 minutes to lapse at room temperature after the hair fibers have been styled in the desired manner;
   F. rinsing the head of hair; and
   G. combing the permanently styled head of hair to attain the desired visual appearance.

* * * * *